(12) United States Patent
Kawahara et al.

(10) Patent No.: US 6,348,152 B1
(45) Date of Patent: Feb. 19, 2002

(54) MEDICAL MATERIAL CONTAINING FLUORINATED POLYSULFONE HAVING EXCELLENT ANTITHROMBOTIC ACTIVITY

(75) Inventors: Hiroaki Kawahara; Satoru Ohmori; Takeyuki Kawaguhi, all of Yamaguchi (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/529,169

(22) PCT Filed: Oct. 8, 1998

(86) PCT No.: PCT/JP98/04553

§ 371 Date: Apr. 10, 2000

§ 102(e) Date: Apr. 10, 2000

(87) PCT Pub. No.: WO99/19381

PCT Pub. Date: Apr. 22, 1999

(30) Foreign Application Priority Data

Oct. 9, 1997  (JP) .............................................. 9-277020
Mar. 16, 1998 (JP) ........................................... 10-065497

(51) Int. Cl.[7] ........................ B01D 13/00; C08L 81/06; A61K 31/795
(52) U.S. Cl. ........................... 210/500.24; 210/500.23; 210/500.41; 523/122; 524/41; 525/181; 525/189; 525/453; 525/535; 525/543; 528/171; 528/174; 528/401
(58) Field of Search ....................... 210/500.23, 500.24, 210/500.41; 523/122; 524/41; 525/181, 189, 453, 543, 535; 528/171, 174, 401

(56) References Cited

U.S. PATENT DOCUMENTS 4,971,695 A * 11/1990 Kawakami et al. .... 210/500.41
5,969,082 A    10/1999 Kuwahara et al. ........... 523/171

FOREIGN PATENT DOCUMENTS

| JP | 51-194    | 1/1976  |
| JP | 54-77497  | 6/1979  |
| JP | 2-45062   | 2/1990  |
| JP | 4-75052   | 3/1992  |
| JP | 7-63901   | 3/1995  |
| JP | 8-302018  | 11/1996 |
| JP | 9-234244  | 9/1997  |
| JP | 10-212347 | 8/1998  |

* cited by examiner

Primary Examiner—Peter Szekely
(74) Attorney, Agent, or Firm—Sughrue, Mion, Zinn Macpeak & Seas, PLLC

(57) ABSTRACT

A medical material composed of a poly(alkyl aryl ether) sulfone copolymer (A) and a thermoplastic polymer (B), such as cellulose triacetate, and being used in contact with the blood, wherein the concentration of the copolymer (A) is at least 40% by weight at least near the surface of a part having a surface to be used in contact with the blood and the copolymer (A) is a specified polysulfone bearing fluorine atoms and polyalkyl ether units and which is suitable for a hollow fiber membrane for artificial kidneys, and the like.

21 Claims, No Drawings

MEDICAL MATERIAL CONTAINING FLUORINATED POLYSULFONE HAVING EXCELLENT ANTITHROMBOTIC ACTIVITY

TECHNICAL FIELD

The present invention relates to a medical material containing fluorinated polysulfone having excellent in antithrombogenic properties. More particularly, the present invention relates to a medical material for use in contact with blood, suitable for a hollow fiber membrane for artificial kidneys or the like, the material containing a polysulfone having fluorine atom(s) and polyalkyl ether unit(s).

BACKGROUND ART

Synthetic polymer materials have been widely used for medical materials including artificial organs and catheters in recent years. Typical materials thereof include hydrophobic polymers such as polyesters, polyvinyl chloride, polystyrene, silicone resins, polymethacrylic esters and fluorine-containing resins and hydrophilic polymers such as polyvinyl alcohol, polyether urethanes (segmented polyurethanes, SPU), poly(2-hydroxyethyl methacrylate) and polyacrylamide as medical polymer materials. Most of the conventional materials have mainly attracted attention to physical and mechanical characteristics and have been used; however, SPU is known for its relatively excellent antithrombogenic properties.

Meanwhile, along with the progress of medical technologies, there have been more and more chances for materials to contact with biotissues or blood, and great problems about the bioaffinity of the materials have been caused. Particularly, the adsorption of biocomponents such as proteins and blood corpuscles on material surfaces and denaturation thereof not only cause normally unrecognized adverse effects such as thrombogenesis or inflammatory reactions on the side of living bodies but also are related to degradation of the materials. Therefore, these are important problems of medical materials which must be fundamentally and urgently solved. As for the prevention of blood coagulation on the material surfaces, blood anticoagulants represented by heparin have hitherto been continuously administered. Effects of long-term administration of the heparin (side effects such as hepatopathy, e.g. lipid dysbolism, prolonged bleeding time or allergic reactions), however, have become problems in recent years. Particularly, the development of blood contacting materials without requiring anticoagulants has been strongly desired for hemodialysis therapy for patients suffering from chronic renal failure and undergoing blood purification such as hemodialysis or hemofiltration.

At present, more than 100,000 patients undergo a blood purification in Japan. The principle of the blood purification is based on the contact of blood through a membrane with a dialyzing fluid, diffusion and removal of waste products or metabolites in the blood into the dialyzing fluid and further removal of excessive water by utilizing a pressure difference. A blood purifier is used when purifying the blood. The blood purifier comprises a blood circuit of bundled hollow fibers stored in a housing and has a structure for making the blood flow through the interior of the hollow fibers and the dialyzing fluid through the exterior thereof. Regenerated cellulose membranes, especially the regenerated cellulose membranes produced by a cuprammonium method have heretofore been widely used as a dialysis membrane material for the blood purifier and have played a great role in the prolongation of the life and rehabilitation of patients suffering from renal failure along with the progress in a dialysis apparatus or dialytic technologies. This is due to nothing but the fact that the regenerated cellulose membranes have excellent dialysis performances and mechanical strength and further high safety supported by the results of actual long-term use. On the other hand, in spite of progress made in hemodialysis therapy, various problems caused by the dialysis remain yet unsolved in fact. One of the main problems is temporary leukopenia due to the activation of complements contained in blood by a cellulose polymer. Another is various side effects regarded as being caused by long-term administration of a large dose of anticoagulants. As described above, blood anticoagulants typified by heparin have been continuously administered in order to suppress a blood coagulation reaction in a blood purifier when carrying out the hemodialysis. However, under the current circumstances where the solute removal performances of the blood purifier have been improved and the prolongation of life even to 20 years is now possible, problems caused by the use of the heparin have successively been pointed out. Particularly, it is revealed that the long-term administration of the heparin causes complication of side effects such as hepatopathy, e.g. lipid dysbolism, prolonged bleeding time or allergic reactions. From the point of view, the development of a blood purifier which-reduces the amount of anticoagulants used or which does not cause blood coagulation even without the use thereof at all during the blood purification therapy, i.e. the blood purifier having antithrombogenic properties has been ardently desired. Furthermore, the antithrombogenic blood purifier enables the portable use of the whole apparatus, promotes the rehabilitation of a patient confined to the hospital for about 5 hours, 2 to 3 days a week and is connected with an enhancement of his or her quality of life.

Several methods have been proposed for suppressing the activation of complements or improving the antithrombogenic properties without impairing other excellent performances of the regenerated cellulose membrane. For example, as for the suppression of the activation of complements, reports have been made of methods for fixing a polymer having a tertiary amino group onto the surface of the membrane, a method for grafting a hydrophilic polymer such as a polyethylene oxide chain onto the surface thereof by covalent bonding or the like, and effects on the suppression of the activation of complements to some extent have been confirmed. The methods, however, are still insufficient in terms of the suppression of blood coagulation (antithrombogenic properties), and there are many problems in aspects of an increase in cost due to complicatedness of methods for fixing and difficulties in obtaining of homogeneous fixed surface layers. The methods have not yet been put to practical use (for example, Japanese Laid-Open Patent Application No. 51-194/1976 and Japanese Laid-Open Patent Application No. 54-77497/1979).

All the above hydrophobic polymer materials such as polyvinyl chloride or polymethacrylic esters and hydrophilic polymer materials such as polyvinyl alcohol or poly(2-hydroxyethyl methacrylate) are not satisfactory in terms of mechanical strength, bioaffinity or the like.

Although the segmented polyurethanes suppress the adhesion of platelets by a micro-phase separation structure between a hard aromatic urethane bonding site and a soft polyether bonding site, the effects are not always sufficient. Particularly, since a partial structure of hydrogen bonding such as urethane bonding or urea bonding has strong interaction between polar groups of the main chain though it contributes to an improvement in rigidity of a molecular chain, the hydration of water molecules capable of reducing the hydrophobic interaction is inhibited. Therefore, it has been reported that the denaturation of proteins is induced and the adhesion of platelets is promoted when the proteins contained in blood are adsorbed. Generally speaking, polar sites such as hydroxyl groups or amino groups naturally induce the activation of complements (the second route) in contact with blood and provide a factor in thrombogenesis due to the promotion of fibrin ation.

Furthermore, it has recently been reported that a membrane comprising synthetic polymers such as a polysulfone or a polyether sulfone are more improved in blood compatibility such as suppression of the activation of complements than that of regenerated cellulose membranes. The antithrombogenic properties, however, are insufficient, and a reduction in the use of anticoagulants does not result.

A cellulose triacetate membrane which is a semisynthetic polymer has advantages of the cellulose and synthetic polymers and manifests a higher ability to suppress the activation of complements than that of the regenerated cellulose, and its water permeability and material permeability are well balanced at the same time. Since the cellulose triacetate membrane has a sufficient mechanical strength, pinholes are hardly formed. Therefor, research and development of the cellulose triacetate membrane is now under way as a material for dialysis membranes in place of the regenerated cellulose. Sufficient performances have been confirmed even by therapeutical and clinical results. The cellulose triacetate membrane, however, is insufficient in terms of antithrombogenic properties, and the development of a novel antithrombogenic membrane capable of reducing the use of anticoagulants is desired.

Japanese patent publication No. 4-75052/1992 discloses a permselective hollow fiber for hemodialysis which is prepared by melt spinning a block copolymer comprising condensed hydrophobic polymer components having a water absorption percentage of 1.0% or below and a polyoxyalkylene and applying orientation in the longitudinal direction of the fiber by drafting or drawing. Polysulfones are disclosed as one of the above condensed hydrophobic polymer components; however, nothing is specifically disclosed.

Japanese Laid-Open Patent Application No. 8-302018/1996 discloses a polysulfone/polyether block copolycondensate having a recurring structural unit such as the following formula (1):

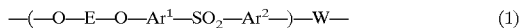
—(—O—E—O—Ar¹—SO₂—Ar²—)—W—    (1)

wherein E denotes a bivalent diphenolate group; $Ar^1$ and $Ar^2$ denote each the same or different bivalent aromatic group having 6 to 50 carbon atoms; W denotes a polyether, a polythioether or a polyacetal having at least two hydroxyl groups and an average molecular weight ($M_n$) of 400 to 30,000, with the proviso that the ratio of the group W in the whole block copolymer corresponds to 5 to 99% by weight. The block copolycondensate is different from the poly(alkyl aryl ether)sulfone copolymer which is an object of the present invention of this application in that the recurring structural unit represented by the above formula (1) has the units in a ratio of 1 mole of —Ar¹—SO₂—Ar²— to the sum total of 2 moles of the group E and group W.

By the way, the present inventors et al. have made research on polymer materials excellent in blood compatibility and especially good in antithrombogenic properties, and it has been found that a specific polysulfone and a specific polyketone containing a polyalkyl ether unit manifest high antithrombogenic properties (European Patent Application No. EP 781795). The performances of said polymers, however, are not considered as sufficient in aspects of stability.

An object of the present invention is to provide a medical material excellent in antithrombogenic properties for use in contact with blood.

Another object of the present invention is to provide a medical material comprising a novel fluorine atom-containing poly(alkyl aryl ether)sulfone copolymer (A) as a part of the material for use in contact with blood.

A further object of the present invention is to provide a medical material composed of a polymer composition comprising the above copolymer (A).

A still another object of the present invention is to provide a novel fluorine atom-containing poly(alkyl aryl ether) sulfone copolymer (A) constituting the above medical material.

A still further object of the present invention to provide an industrially advantageous method for producing the medical material of the present invention.

Additional objects and advantages of the present invention will be apparent from the following description.

According to the present invention, the above objects of the present invention are achieved by a medical material for use in contact with blood, excellent in antithrombogenic properties, the material comprising a poly(alkyl aryl ether) sulfone copolymer (A) and a thermoplastic polymer (B) other than the copolymer (A), wherein the concentration of said copolymer (A) in the vicinity of the surface of a portion at least having a surface for use in contact with blood is at least 40% by weight, and said copolymer (A) is a fluorine atom-containing poly (alkyl aryl ether)sulfone copolymer (A) substantially comprising (a) constituent units represented by the following formulae (1) to (3):

—(—Ar¹—SO₂—Ar²—O—)—    (1)

—(—Ar³—Y—Ar⁴—O—)—    (2)

—(—RO—)ₖ—    (3)

(in which $Ar^1$ and $Ar^2$ are each independently a bivalent aromatic group having 6 to 30 carbon atoms which may have a substituent group; $Ar^3$ and $Ar^4$ are each independently a bivalent aromatic group having 6 to 30 carbon atoms which may have a substituent group; Y is an alkylene group having 1 to 18 carbon atoms, at least one of its hydrogen atoms being substituted with a fluorine atom; R is an alkylene group having 2 or 3 carbon atoms or a combination of an alkylene group having 2 or 3 carbon atoms and an alkylene group having 4 carbon atoms; and k is a numeral which ensures that the molecular weight of a unit represented by —(—RO—)ₖ— is in the range of 400 to 20,000), the constituent unit represented by the above formula (3) accounting for 10 to 90% by weight based on the total amount of the constituent units represented by the above formulae (1), (2) and (3), the constituent unit represented by the above formula (1) accounting for 30 to 60 mole % based on the constituent unit represented by the above formula (2), and the copolymer having a reduced viscosity of at least 0.5 dl/g measured at a concentration of 1.2 g/dl in a mixed solvent of phenol and 1,1,2,2-tetrachloroethane at a weight ratio of 6/4 at 35° C.

The medical material for use in contact with blood of the present invention comprises the poly(alkyl aryl ether) sulfone copolymer (A) and a thermoplastic polymer (B) other than the copolymer (A). According to the present invention, the concentration of said copolymer (A) in the vicinity of the surface of the portion having the surface used in contact with blood is at least 40% by weight to thereby provide the medical material excellent in antithrombogenic properties.

The surface of the portion having at least the surface used in contact with blood may be composed of a composition of, for example, said copolymer (A) and said thermoplastic polymer (B) or may be composed of said copolymer (A) formed on said thermoplastic polymer (B). For example, coating methods using a solvent, melting methods or the like can be cited as the method for forming the surface.

The poly(alkyl aryl ether)sulfone copolymer (A) of the present invention substantially comprises constituent units represented by the above formulae (1), (2) and (3):

$Ar^1$ and $Ar^2$ in the formula (1) are each the same or different and are each a bivalent aromatic group having 6 to 30 carbon atoms which may have a substituent group. For example, p-phenylene, m-phenylene, 2,6-naphthylene, 2,7-naphthylene, 1,4-naphthylene, 1,5-naphthylene, 4,4'-biphenylene, 2,2'-biphenylene, 4,4'-oxylenediphenylene, 4,4'-isopropylidenediphenylene, 4,4'-isopropylidene-2,2',6,6'-tetramethyldiphenylene and 4,4'-sulfonyldiphenylene can be exemplified as the aromatic groups. Among the groups, aromatic hydrocarbon groups having 6 to 10 carbon atoms such as p-phenylene, m-phenylene or 2,6-naphthylene are preferred, and p-phenylene is more preferred. Ari and $Ar^2$ are preferably p-phenylene at the same time.

$Ar^1$ and $Ar^4$ in the formula (2) are each the same or different and are each a bivalent aromatic group having 6–30 carbon atoms which may have a substituent group. The same aromatic groups as those cited in the above formula (1) can be exemplified as the aromatic groups.

Y in the formula (2) is an alkylene group having 1 to 18 carbon atoms in which at least one of hydrogen atoms is substituted with fluorine atom and, for example, 1,3-difluoroisopropylidene, 1,1,3-trifluoroisopropylidene, 1,3,3-trifluoroisopropylidene, 1,1,3,3-tetrafluoroisopropylidene, 1,1,1,3,3-pentafluoroisopropylidene, 1,1,3,3,3-pentafluoroisopropylidene, 1,1,1,3,3,3-hexafluoroisopropylidene, trifluoromethylene and monofluoroisopropylidene are cited. Y is preferably an alkylene group having 2 to 6 carbon atoms in which at least one of hydrogen atoms is substituted with fluorine atom, and the number of fluorine atoms is preferably 1 to 6, more preferably 2 to 5. The number of carbon atoms in the alkylene group is more preferably 2 or 3. Among the groups, 1,1,1,3,3,3-hexafluoroisopropylidene and trifluoromethylene are especially preferred as Y.

In the formula (3), R is an alkylene group having 2 or 3 carbon atoms or a combination of the alkylene group having 2 or 3 carbon atoms with an alkylene group of 4 carbon atoms. For example, ethylene, propylene and trimethylene can be exemplified as the alkylene group having 2 or 3 carbon atoms. Among the groups, an ethylene group is especially preferred as R. Tetramethylene group can be exemplified as the alkylene group having 4 carbon atoms. R may be a single structure or may be a structure of a combination of two or more kinds. As for the combination of the alkylene group having 2 or 3 carbon atoms with the alkylene group having 4 carbon atoms, the ratio of the alkylene group of 4 carbon atoms is 80 mole % or below, preferably 60 mole % or below. k is a numeral which ensures that the molecular weight of a unit represented by —(—RO—)k— is in the range of 400 to 20,000. The molecular weight of the polyoxyalkylene structural unit is preferably 600 to 15,000, more preferably 800 to 10,000, especially preferably 1,000 to 6,000.

The above copolymer (A) preferably substantially comprises (a) the following formulae (11) to (31):

  (11)

  (21)

  (31)

wherein $Ar^{11}$ and $Ar^{21}$ are each independently a bivalent aromatic hydrocarbon group having 6 to 10 carbon atoms which may have a substituent group; $Ar^{31}$ and $Ar^{41}$ are each independently a bivalent aromatic hydrocarbon group having 6 to 10 carbon atoms which may have a substituent group; Y is an alkylene group having 2 to 6 carbon atoms in which at least one of hydrogen atoms is substituted with fluorine atom; R is an ethylene group; k is a numeral which ensures that the molecular weight of a unit represented by —(—RO—)$_k$— is in the range of 400 to 20,000.

Among the groups, $Ar^1$, $Ar^2$, $Ar^3$ and $Ar^4$ are each especially preferably p-phenylene group, and Y is especially preferably 1,1,1,3,3,3-hexafluoroisopropylidene.

Furthermore, in the above copolymer (A), the content of the structural unit —(OR—)$_k$— in the formula (3) is 10 to 90% by weight based on the total weight of the recurring units represented by the formulae (1) and (2). In the case of less than 10% by weight, the hydrophobicity of the copolymer is too high, and the wetting with water is insufficient when formed into a dry film. In the case of higher than 90% by weight, the hydrophilicity of the resulting copolymer is too high, with the result that elution into water and remarkable swelling occur and mechanical strength becomes insufficient. The content of the structural unit —(—OR—)$_k$— is preferably 30 to 80% by weight, more preferably 40 to 70% by weight on the same basis.

The above copolymer (A) includes copolymers comprising recurring units represented by, for example the following formulae (4) and (5):

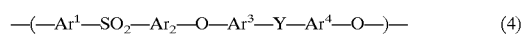  (4)

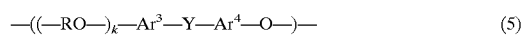  (5)

or recurring units represented by the following formulae (4) and (6):

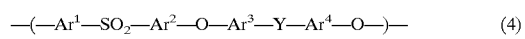  (4)

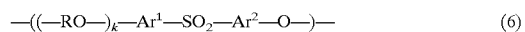  (6)

or recurring units represented by the following formulae (7) and (6):

  (7)

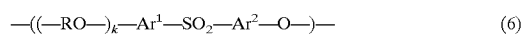  (6)

wherein the definitions of $Ar^1$, $Ar^2$, $Ar^3$, $Ar^4$, Y, R and k are the same as those described above.

Furthermore, the copolymer (A) of the present invention has a reduced viscosity of at least 0.5 dl/g measured at a concentration of 1.2 g/dl in a mixed solvent of phenol and 1,1,2,2-tetrachloroethane in a weight ratio of 6/4 at 35° C. In the case of less than 0.5 dl/g, the mechanical strength of the resulting copolymer becomes insufficient. The reduced viscosity is preferably at least 1.0 dl/g, more preferably 1.0 to 3.0 dl/g.

The copolymer (A) of the present invention may contain other components as a copolymerization component within the range without essentially changing properties thereof (for example, 20% by weight or less, preferably 10% by weight or less). The other components to be copolymerized include, for example, polyesters comprising ethylene terephthalate unit, butylene terephthalate unit or ethylene naphthalate unit as a main recurring unit, polyether sulfones comprising diphenyl sulfone as a main recurring unit, polysulfones comprising a condensate of the diphenyl sulfone with bisphenol A as a main recurring unit, polycarbonates comprising a carbonic ester of the bisphenol A as a main recurring-unit or monomeric components constituting the components.

When the above copolymer (A) is mixed and used with the other thermoplastic polymer (13) described below, the compatibility of the copolymer (A) with the thermoplastic polymer (B) is improved, and the antithrombogenic properties and mechanical characteristics of the medical material comprising the resulting polymer composition are good if the solubility parameter is within a specific range. The compatibility of the copolymer (A) with the thermoplastic polymer (B) is insufficient if the δ is much smaller or much larger than the range, and both are macroscopically (in a size of the micron order or above) separated to thereby unfavorably deteriorate the mechanical characteristics thereof without forming a finely mixed and dispersed blended material of both (in a size of the submicron order).

δ is herein represented by the following formula (8):

$$\delta = \rho \cdot \Sigma F_i / M \tag{8}$$

wherein ρ is the density of the polymer; M is the molecular weight of the recurring unit structure of the polymer; $\Sigma F_i$ is the sum total of molar attraction force constants and the total of values intrinsic to each partial structure.

That is, the respective variables are publicly known for polymers wherein the physical properties are known, and δ can readily be determined [for example, a book "Polymer Blend" under joint authorship of Saburo Akiyama, Takashi Inoue and Toshio Nishi, published by CMC Co., Ltd. and literature: K. L. Hoy, J. Paint Technol., 42, 76 (1970)]. δ of general polymers varies with the molecular structure and the copolymer composition when the polymer is the copolymer. The copolymer (A) having a value of δ closer to that of various polymers (B) is considered as more easily compatible with the polymers (B). In general, it is thought that mechanical characteristics of one of polymers in a polymer blend having a higher compatibility are hardly changed.

When the polymer (B) is, for example, a polysulfone or a polyaryl ether sulfone, δ is preferably 9.0 to 14.0.

When the polymer (13) is polyvinyl chloride, δ is preferably 9.0 to 10.4.

When the polymer (B) is a polyurethane, δ is preferably 9.0 to 10.3.

When the polymer (B) is polymethyl methacrylate, δ is preferably 9.0 to 10.3.

The copolymer (A) of the present invention can be produced by a conventionally known method, for example, in the manner as described below:

(i) thermally reacting a bis(haloaryl)sulfone with an α, ω-bis(haloalkoxy)polyoxyalkylene and a dihydroxyaryl compound in the presence of an alkali or (ii) thermally reacting a bis(haloaryl)sulfone with an α, ω-bis(hydroxy)polyoxyalkylene and a dihydroxyaryl compound in the presence of an alkali.

The method for production, however, is not especially limited thereto.

The copolymer (A) of the present invention thus obtained has an extremely small amount of proteins adsorbed measured by a Micro BCA method when brought into contact with a human blood plasma at 37° C. for 1 hour, that is 0.7 $\mu g/cm^2$ or below and further has excellent adsorption suppressing effects on adhesion or the like of proteins and platelets contained in blood when brought into contact with a blood plasma solution. The reason why the copolymer (A) of the present invention has excellent adsorption suppressing effects is considered as follows. The above copolymer has a polyaryl sulfone unit (hard component) which is a hard site and a hydrophilic polyoxyalkylene unit (soft component) fixed into the polymer main chain, and both the hydrophilic segment and the hydrophobic polyaryl sulfone segment are characterized in not only a thermodynamically but also a macroscopically phase separated surface structure. Since a hydrogen bond donative group is absent in the main chains of the polymer, interaction between the main chains is small and contact of water molecules capable of reducing the hydrophobic interaction readily occurs in a domain of the hydrophilic polyoxyalkylene unit. The selective adsorption of bioproteins on the surface based on the pattern of the domain, therefore, is caused without denaturing the proteins adsorbed on the surface. As a result, the polymer surface is kept in a state of normal proteins adsorbed on the surface in a monolayer to suppress the adhesion of further biocomponents (erythrocytes, leukocytes and platelets). The harmful bioreaction such as activation of complements, thrombogenesis or damage to a cell membrane can be avoided. The amount of proteins adsorbed is desirably as small as possible; however, substantially sufficient effects are manifested when the amount is within the range of 0.3 to 0.7 $\mu g/cm^2$.

The above copolymer (A) of the present invention not only can suitably be used as a protein filtration membrane, a supporting membrane for a permeable membrane, a medical hemodialysis membrane or an agent for imparting antithrombogenic properties to a medical polymer or the like but also is useful as an ultrafiltration membrane, a precision filtration membrane or the like.

According to the present invention, it is therefore definitely shown that the above poly(alkyl aryl ether)sulfone copolymer of the present invention is suitably used for producing the medical material for use in contact with blood.

According to the present invention, the use of the above copolymer (A) of the present invention for producing the medical material for use in contact with blood is provided.

The use includes not only the employment of the copolymer of the present invention as a material for the medical material but also as one component of a polymer composition in combination with a thermoplastic polymer as another material or as a coating material for coating the medical material prepared from other materials. The other materials herein include aromatic polyesters, for example, polysulfones, polyaryl ether sulfones, diacetylcellulose, cellulose triacetate, polyurethanes, polycarbonates or polyethylene terephthalate and thermoplastic polymers, for example, polyethylene, polypropylene, polyvinyl chloride, polystyrene, silicone resins, polyalkyl methacrylates, fluororesin, polyvinyl alcohol, poly(2-hydroxyethyl methacrylate), polyacrylamide, rubber-based elastomers, polyamides or polydimethylsiloxane. One of the materials or two or more thereof together can be used.

The thermoplastic polymer (B) which is a material constituting the medical material is preferably cellulose triacetate, a polysulfone, a polyaryl ether sulfone, polyvinyl chloride, a polyurethane and polymethyl methacrylate.

For example, cellulose triacetate having a number-average molecular weight of 30,000 to 150,000 and a combined acetyl content of 2.8 or above is preferably used as the cellulose triacetate.

A homopolymer or a copolymer of an aromatic polysulfone represented by the following formulae (51) and (52):

  (51)

  (52)

wherein the definitions of $Ar^1$, $Ar^2$, $Ar^3$ and $Ar^4$ are the same as those described above; Z is —$SO_2$— or a bivalent hydrocarbon group of 2 to 10 carbon atoms such as isopropylidene group, is preferred as the polysulfone and polyaryl ether sulfone.

The polymer has a reduced viscosity of preferably 0.5 to 3.0 measured at a concentration of 1.2 g/dl in a mixed solvent of phenol with 1,1,2,2-tetrachloroethane (in a weight ratio of phenol/1,1,2,2-tetrachloroethane of 6/4) at a temperature of 35° C.

Among them, the aromatic polysulfone is preferably a medical grade aromatic polysulfone, for example, (a) an aromatic polysulfone obtained by thermal condensation of 2,2'-bis(4-hydroxyphenyl)propane with 4,4'-dichlorodiphenyl sulfone and having a number-average molecular weight of 20,000 to 30,000 (a specific gravity of 1.24 and a glass transition point of 190° C.), (b) a polyaryl ether sulfone prepared by thermal condensation of 4,4'-dihydroxydiphenyl sulfone with 4,4'-dichlorodiphenyl sulfone and having a number-average molecular weight of 20,000 to 30,000 (a specific gravity of 1.37 to1.60 and a glass transition point of 220° C.) or the like.

The polyurethane may be a material having a number-average molecular weight of 10,000 to 1,000,000 and a medical grade segmented polyurethane widely used as the medical material is especially preferred. The medical segmented polyurethane is developed as a polyurethane material used mainly for medical applications. The polyurethane has structural characteristics wherein the chain of an aliphatic or an aromatic group which is a hard segment is bonded through urethane bonds and an aliphatic polyether or a polyester chain as a soft segment is bonded to the hard segment through the urethane bonds as the structure thereof Both segments of the hard and the soft segments having physicochemically low compatibility are not mutually compatibilized, and a microdomain of phase separation in bulk is formed. The biocompatibility of the polymer is improved by the microdomain, and the polyurethane is used especially for the medical applications. Examples of the cited medical segmented polyurethane include a polyurethane obtained by polyaddition of methylenediphenyl-4,4'-diisocyanate to ethylene glycol and having a number-average molecular weight of 20,000 to 30,000, a polyurethane comprising a soft segment composed of polytetramethylene oxide (PTMO) and a hard segment composed of 4,4'-diphenylmethane diisocyanate (MDI) and ethylenediamine ("Biomer®", manufactured by Ethicon Inc.), a polyurethane comprising PTMO, MDI and butanediol ("Pellethane®" manufactured by Upjohn Co.) or a polyurethane comprising PTMO, a hydrogenated MDI and butanediol ("Tecoflex®" manufactured by Thermo Electron Co.).

A polycarbonate obtained by polycondensation of a bisphenol derivative, for example, 4,4'-isopropylidenediphenol with phosgene or diphenyl carbonate, especially preferably the polycarbonate having a number-average molecular weight of 20,000 to 50,000 is advantageously used as the polycarbonate.

The polyalkyl methacrylates are alkyl esters of polymethacrylic acid and an alkyl group comprising an aliphatic hydrocarbon chain of 1 to 18 carbon atoms can be cited as the alkyl group. Specifically, a linear alkyl group such as methyl, ethyl or propyl group, a branched chain alkyl group such as isopropyl or isobutyl group and/or a cyclic alkyl group such as cyclohexyl group are cited. The alkyl group may be used alone or a plurality thereof may be copolymerized. Among the alkyl groups, a linear alkyl group of 1 to 3 carbon atoms is preferred, and methyl group of 1 carbon atom is more preferred from the aspects of membrane physical properties. The polyalkyl methacrylates used herein are preferably a material which is a medical grade polyalkyl methacrylate having a number-average molecular weight of 10,000 to 1,000,000 without containing impurities or the like. Among the polyalkyl methacrylates, polymethyl methacrylate is preferably used.

A material having a number-average molecular weight of 10,000 to 1,000,000 may be used as the rubber-based elastomer, and a medical grade rubber-based elastomer widely used as the medical material is especially preferred. Examples of the cited medical rubber-based elastomer include a cross-linked natural rubber comprising an isoprenoid skeleton, chloroprene prepared by halogenating a skeleton similar to that of natural rubber, a styrene type rubber-based elastomer such as SES (Kraton G®), SIS (VECTOR®), SBS (KR-10, Styrolux®) or SEBS (Tuftec®) which is an ABA block copolymer of a styrene skeleton as a hard segment and an aliphatic soft segment such as ethylene, isoprene, butadiene or a hydrogenated ethylene butadiene or an ethylene/propylene rubber comprising a crystalline ethylene skeleton as a hard segment and an amorphous propylene or the like as a soft segment.

In a preferred embodiment of the present invention, antithrombogenic properties can be imparted to the thermoplastic polymer (B) while maintaining its properties in order to provide a medical material for use in contact with blood by applying, as the polymer composition, the above thermoplastic polymer (B) in combination with the above poly (alkyl aryl ether)sulfone copolymer (A).

According to the present invention, said copolymer (A) and said thermoplastic polymer (13) may form separate phases without uniformly mixing at a molecular level and present as separate phases in the medical material composed of the polymer composition of said copolymer (A) and said thermoplastic polymer (B). The concentration of said copolymer (A) in the surface part of the material composed of the polymer composition is raised from the average concentration of the above copolymer (A) in said whole polymer composition. This properties are utilized in the present invention.

The vicinity of the surface used in contact with blood preferably comprises 1 to 50% by weight of the copolymer (A) and 99 to 50% by weight of the polymer (3) in the medical material of the present invention. When the amount of the copolymer (A) is less than 1 part by weight, it is unfavorable that sufficient antithrombogenic effects are not obtained due to the too small amount of the copolymer (A) present in the surface of the medical material. When the amount of the copolymer (A) exceeds 99 parts by weight, essential physical characteristics and service conditions unfavorably greatly vary with the kind of the polymer (B). The vicinity of the surface is composed of a polymer composition comprising more preferably 5 to 30% by weight of the copolymer (A) and 70 to 95% by weight of the polymer (B), far more preferably 5 to 20% by weight of the copolymer (A) and 80 to 95% by weight of the polymer (B).

The concentration of the copolymer (A) in the vicinity of the surface in contact with blood is at least 40% by weight, preferably 50 to 90% by weight.

The proportion of the copolymer (A) in the vicinity of the surface is higher than the proportion (concentration) of the copolymer (A) in the whole polymer composition when producing the medical material from, for example, a solution of the polymer composition in an organic solvent. That is, the phase separation may occur as the organic solvent is scattered from the solution to finally provide a medical material at a high concentration of the copolymer (A) in the vicinity of the surface. The vicinity of the surface means a region from the surface to a depth of about 100 Å though it is not strict.

The concentration of the copolymer (A) in the vicinity of the surface can be determined according to the measurement of the surface composition by ESCA. The method for measurement is described in the part of Example.

The polymer composition can be prepared by dissolving, for example, the copolymer (A) and the thermoplastic polymer (B) in a common solvent for dissolving the copolymer (A) and the thermoplastic polymer (B) in a prescribed proportion and then removing the solvent or melt mixing the copolymer (A) with the thermoplastic polymer (B) in the above prescribed proportion.

For example, a cyclic ether-based organic solvent such as tetrahydrofuran, 1,3-dioxolane or 1,4-dioxolane, an amide-based solvent such as N,N'-dimethyformamide (DMF), N,N'-dimethylacetamide (DMAc) or N-methyl-2-pyrrolidone (NMP) and a halogen-based organic solvent such as chloroform or methylene chloride can be cited as the solvent.

Furthermore, according to the present invention, for example, cellulose triacetate, a polysulfone, a polyaryl ether sulfone, polyvinyl chloride, a polyurethane and a polyalkyl methacrylate are preferably cited as the thermoplastic polymer (13) by taking the selectivity and handleability of the solvent for dissolving the above copolymer (A) and the above polymer (B) into consideration.

For example, a rubber-based elastomer, a polyamide, a polyester, a polyurethane, a polyalkyl methacrylate, cellulose diacetate, a polycarbonate, a polyamide and polydimethylsiloxane can be cited as the thermoplastic polymer (B) melt mixable with the above copolymer (A).

According to the present invention, there is provided a method for producing the medical material characterized in that a dope comprising the poly(alkyl aryl ether)sulfone copolymer (A), the thermoplastic polymer (B) and an aprotic polar organic solvent (C) capable of dissolving both the components (A) and (B) at the total concentration of the above components (A) and (3) of 1 to 30% by weight is prepared and formed into a thin membrane, which is then subjected to a wet or a dry molding method to produce the medical material having a thickness of 1 mm or below and a portion used in contact with blood.

Tetrahydrofuran, 1,3-dioxolane, 1,4-dioxane, dimethylformamide, dimethylacetamide, N-methyl-2-pyrrolidone, dimethyl sulfoxide, methylene chloride and chloroform are preferably used as the aprotic polar organic solvent.

In order to form the dope into the thin membrane, for example, the formation of the thin membrane can be carried out by casting the dope onto a substrate to provide a filmy form or by spinning the dope into a hollow fibrous form. The total concentration of the components (A) and (B) in the dope is preferably 5 to 20% by weight, more preferably 10 to 15% by weight when casting the dope and preferably 5 to 30% by weight, more preferably 10 to 20% by weight, especially preferably 13 to 14% by weight when spinning the dope into the hollow fibrous form.

The dope is formed into the thin membrane, and the aprotic polar organic solvent is then removed by a wet or a dry method to afford the medical material as a self-supporting molded product.

The wet method is a method for treating the thin membrane of the dope in water/aprotic polar organic solvent and then in water to thereby removing the aprotic polar organic solvent in the dope. The dry method is a method for treating the thin. membrane of the dope at normal temperatures under atmospheric pressure or at 40 to 50° C. under a vacuum of about 1 to 30 mmHg and thereby similarly removing the aprotic polar organic solvent in the dope.

The resulting thin membrane which is the portion of the medical material used in contact with blood has a thickness of preferably 1 $\mu$m to mm, and the thin membrane having a membrane thickness of 10 to 50 $\mu$m is especially advantageous.

When all of the above medical materials of the present invention are allowed to contact with a phosphoric acid buffer solution of human platelet-poor plasma (PPP) at a concentration of 5% by weight at 37° C. for one hour, the amount of proteins adsorbed on the surface thereof is preferably 0.8 $\mu$g/cm$^2$ or below, more preferably 0.6 $\mu$g/cm$^2$ or below (expressed in terms of albumin according to the Micro BCA method). When the amount of the proteins adsorbed at the time of contact with the blood plasma is larger than 0.8 $\mu$g/cm$^2$, the subsequent adhesion and activation of platelets cannot sufficiently be suppressed. Thereby, the thrombogenesis readily proceeds. Although the amount of the protein adsorbed is desirably smaller, practically sufficient effects are manifested when the amount is within the range of 0.3 to 0.7 $\mu$g/cm$^2$, preferably 0.3 to 0.5 $\mu$g/cm$^2$.

In the case of, for example, a hollow fiber membrane, the medical material of the present invention has a number of the hollow fiber membranes causing thrombin on the surface of preferably 4 (10%) or below, more preferably 2 (5%) or below when dipping a bundle of the 40 bundled hollow fiber membranes in nonheparin blood collected from the human brachial part, allowing the dipped bundle to stand at normal temperature for 4 hours and then washing the bundle.

For example, a hollow fiber for artificial kidneys, a hollow fiber for artificial lungs, a catheter, an artificial blood vessel, a blood-collecting tube, a tube for blood circuits, a blood container, a hemodialysis membrane, a blood plasma separation membrane and a medical suture thread can be cited as the medical material of the present invention.

At least the portion in contact with blood of the medical material of the present invention is composed of the above polymer composition and coated with, for example, a thin membrane comprising said polymer composition. The portion in contact with blood herein refers to the surface of the material in contact with blood and its vicinity. For example, at least the inner surface where blood flows may be composed of the above polymer composition when used as a dialysis membrane for artificial kidneys.

The reason why the polymer composition comprising the poly(alkyl aryl ether)sulfone copolymer (A) and the polymer (B) in the present invention manifests excellent blood compatibility is assumed to be as follows:

As described above, the copolymer (A) of the present invention manifests excellent antithrombogenic properties, and the polymer composition of the present invention comprising the copolymer (A) may be kept in a state of phases macroscopically separated from the other thermoplastic polymer (B) which is another component of the polymer composition and a medical polymer element. When preparing the polymer composition, for example, when removing the solvent in the wet blend, the polyoxyalkylene unit of the above copolymer may be rather oriented in the interface between the polymer composition and the bulk (the interface of air/polymer composition, the interface of water/polymer composition or the like) than the interior of the polymer composition in order to stabilize the interfacial free energy in the polymer composition. Thereby, the above copolymer (A) may be oriented over the most part of the water contact interface in the presence of water (blood) to form a hydrogel layer of the hydrated copolymer. Accordingly, the biocomponents such as proteins or blood corpuscles are hardly adsorbed, and the denaturation of the proteins adsorbed, the adhesion and activation of contacted platelets can be suppressed. It is assumed that the activation of complements and damage to a cell membrane can be avoided because the number of polyoxyalkylene free terminal chains, the number of free hydroxyl group terminals and the like are markedly reduced.

Effects of the Invention

The poly(alkyl aryl ether)sulfone copolymer of the present invention is excellent in antithrombogenic properties in itself and is capable of providing a medical material hardly adsorbing biocomponents such as proteins and blood corpuscles, suppressing the adsorption of proteins over a long period and having ultrahigh stability with time. Furthermore, the copolymer is capable of suppressing the denaturation of proteins adsorbed and adhesion and activation of contacted platelets. The antithrombogenic properties can be imparted to said medical material by compounding with other medical polymers. It is assumed that the activation of complements and damage to a cell membrane can be avoided because the number of the polyoxyethylene free terminal chains, the number of free hydroxyl group terminals and the like in the above copolymer are small. The copolymer and polymer composition of the present invention, therefore, are useful as the medical material to be the main object for use in direct contact with blood components and can be used as, for example, artificial kidneys, artificial blood vessels, artificial lungs, hemodialysis membranes, blood bags, catheters or blood plasma separation membranes. When used as the material, the above copolymer and the above polymer composition themselves can be not only used as the material and molded into hollow fibers, sheets, films or tubes but also dissolved in a solvent to coat the surfaces of the various materials with the solution and modify only the blood contact surfaces.

EXAMPLES

The present invention is described in more detail hereinafter by the following referential examples and examples, provided that the examples are not intended as a definition of the present invention. "Parts" in the examples means "parts by weight" unless otherwise specified.

The reduced viscosity ($\eta_{sp/c}$) of the poly(alkyl aryl ether) sulfone copolymer (A) was measured by dissolving 120 mg of the copolymer in 10 ml of a mixed solvent of phenol with 1,1,2,2-tetrachloroethane (in a weight ratio of 6/4 of the phenol/1,1,2,2-tetrachloroethane) and using the resulting solution at 35° C.

A polyaryl ether sulfone (PES) obtained by thermal reaction of 4,4'-dihydroxydiphenyl sulfone with 4,4'-dichlorodiphenyl sulfone and cellulose triacetate (TAC) having an acetyl content of 2.8 were respectively used as the polymer (B).

The number-average molecular weight was determined by the GPC measurement (using a developing solvent of chloroform and expressed in terms of polystyrene).

The quantitative evaluation of proteins adsorbed was carried out by the Micro BCA method. This method is a protein assaying method using a Micro BCA kit (Micro BCA Assay Reagent Kit, manufactured by Pierce Co., Ltd.) using copper ions and a BCA protein detecting reagent represented by the following structure: Since only the copper ions reduced to a valence of 1 by the proteins present in a sample are allowed to cause a chelating reaction with the reagent thereby to develop a color (at 570 nm), the concentration of the proteins (expressed in terms of albumin) can be determined by measuring the absorbance of the sample.

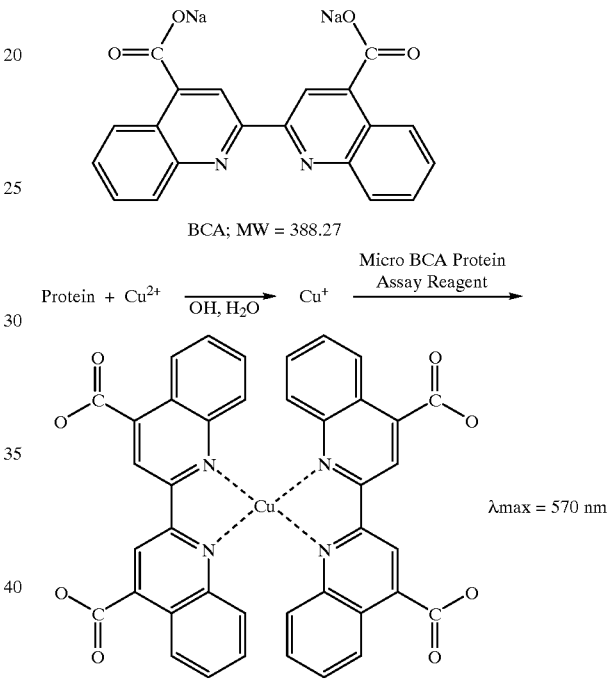

The shape factor of platelets adhered is a value obtained by quantifying the degree of deformation according to the activation of the platelets adhered. The deformation state of the platelets is classified into four stages including the undeformed state as the first stage and the number of the platelets in each state is multiplied by the number of the stage. The sum total is then divided by the total number of the platelets adhered to provide the shape factor. If all the platelets adhered are undeformed, the shape factor is 1. If all the platelets adhered cause the deformation of the fourth stage, the factor is 4.

The surface composition by the ESCA was determined by cutting a film into the form of a disk having a diameter of 1 cm to give a measurement sample. ESCA LAB-200 manufactured by VG Co., Ltd. was used as a measurement instrument. The sample was irradiated with $MgK_\alpha$ radiations so as to provide a photoelectron takeout angle of 45°, and scanning was conducted. The measurement was made on the surface (the front side) brought into contact with the air interface at the time of casting.

A piece of 5×5 mm size was cut from a sample subjected to gold vapor deposition and fixed onto a sample plate made of copper to give an observation sample, which was used to take an SEM photograph and make the surface observation by using an SEM (S-510 manufactured by Hitachi, Ltd).

Referential Example 1

Synthesis of α, ω-bis(2-chloroethoxy)-polyoxyethylene

Into an Erlenmeyer flask with ground-glass joints, were charged 30 parts of polyoxyethylene glycol (#2000), 3.2 parts of pyridine and 150 parts of dehydrated chloroform, and stirring was carried out to prepare a uniform solution. A mixture solution containing 2.4 parts of thionyl chloride and 15 parts of dehydrated chloroform was then added dropwise to the uniform solution under cooling with ice for 30 minutes. The cooling with ice was then removed to raise the solution temperature to room temperature. The stirring was subsequently continued for another 8 hours. The chloroform was distilled off under a reduced pressure. Additional 15 parts of new thionyl chloride was further added, and the resulting solution was dried by distillation under heating for 24 hours. Thereafter, the excess thionyl chloride was distilled off under a reduced pressure, and the residue was dissolved in 300 parts of new chloroform. The prepared solution was washed with 200 parts of a saturated saline solution three times and subsequently washed with 200 parts of pure water once to separate the chloroform layer, which was dried over anhydrous sodium sulfate overnight. The chloroform was distilled off, and the resulting oily substance was immediately solidified at room temperature. The obtained solid was dissolved in 40 parts of acetone under heating and reprecipitated with 200 parts of diethyl ether to afford 28.8 parts of white powdery crystals. The melting point of the product was 50.5 to 53.5° C., and it was confirmed from an IR (infrared spectroscopy) chart that the compound was α, ω-bis(2-chloroethoxy)polyoxyethylene (a number-average molecular weight of 2,000).

Synthesis Example 1

Preparation 1 of Poly(alkyl aryl ether)sulfone Copolymer

Into an Erlenmeyer flask having nitrogen introducing and discharging ports, were charged 16.80 parts of 4,4'-hexafluoroisopropylidenediphenol, 11.90 parts of bis(4-chlorophenyl)sulfone and 25.95 parts of α, ω-bis(2-chloroethoxy)polyoxyethylene (a number-average molecular weight of 3,035) previously freed of coexisting water by azeotropic distillation with toluene, 200 ml of toluene, 100 ml of N,N-dimethylacetamide and 8.625 parts of potassium carbonate, and the resulting mixture was then led to a Dean-Starks trap to carry out nitrogen replacement. The mixture was heated at 115 to 125° C. under reflux for 16 hours. After conforming that the outflow of water caused by the reaction was completed, 200 ml of N,N-dimethylacetamide was newly added in the form making up for the reduction in amount of the toluene while distilling off the toluene for 8 hours. The interior of the flask was replaced with nitrogen, and the contents were further heated at 165 to 180° C. under stirring for 20 hours to cause a reaction. After the reaction, the whole was emptied into 3,000 ml of ion-exchanged water under stirring, washed and then washed with 3,000 ml of new ion-exchanged water under stirring for 2 hours. The operations were repeated three times. The polymer was subsequently washed with 3,000 ml of an aqueous solution of hydrochloric acid at a concentration of 0.1% by weight under stirring for 8 hours to completely deactivate and elute the residual alkali catalyst into water. The resulting polymer was further washed with new 3,000 ml of ion-exchanged water under stirring for 2 hours and dehydrochlorinated. The operations were repeated three times. The obtained polymer was vacuum dried at 80° C. for 24 hours, then extracted with chloroform, filtered and dried. The dried polymer in an amount of about 92% (about 48 g) of the theoretical yield was finally obtained.

The reduced viscosity and number-average molecular weight of the finally obtained polymer were measured, and the results are shown in Table 1.

Synthesis Examples 2 to 9 and 11

Preparation 2 of Poly(alkyl aryl ether)sulfone Copolymers

Various copolymers were synthesized in the same manner as that in the above Synthesis Example 1. Polysulfone copolymers without containing fluorine atoms were synthesized at the same time, and the obtained results are collectively shown in Table 1.

Synthesis Example 10

Preparation 3 of Poly(alkyl aryl ether)sulfone Copolymer

Synthesis was carried out according to the above Synthesis Example 1, except that 12.848 parts of 4'-hexaisopropylidenediphenol (manufactured by Central Glass Co., Ltd.) and 14.358 parts of bis(4-chlorophenyl)sulfone (manufactured by Lancaster), 35.37 parts of α, ω-bis(2-hydroxy)polyoxyethylene #3000 (polyethylene glycol, a number- average molecular weight of 3,000 manufactured by NOF CORPORATION) previously freed of coexisting water by azeotropic distillation with toluene, 15 parts of toluene, 20 parts of N,N-dimethylacetamide and 8.28 parts of potassium carbonate (manufactured by Kanto Chemical Co., Inc.) were used, and about 56 g of the polymer was obtained.

TABLE 1

| Synthesis Example | Polymer[1] | PEO copolymerization ratio (wt. %) | Number-average molecular weight | $\eta_{sp/c}$ | $\delta^{[2]}$ |
|---|---|---|---|---|---|
| 1 | PEO3000(50)-co-PFS(50) | 50 | 25,000 | 0.85 | 10.20 |
| 2 | PEO3000(60)-co-PFS(40) | 60 | 28,000 | 0.95 | 10.15 |
| 3 | PEO2000(50)-co-PFS(50) | 50 | 19,000 | 0.78 | 10.23 |
| 4 | PEO2000(60)-co-PFS(40) | 60 | 22,000 | 0.82 | 10.19 |
| 5 | PEO3000(50)-co-PES(50) | 50 | 25,000 | 1.03 | 11.31 |
| 6 | PEO3000(60)-co-PFS(40) | 60 | 31,000 | 1.15 | 10.15 |
| 7 | PEO3000(50)-co-PFS(50) | 60 | 33,000 | 1.21 | 10.20 |

TABLE 1-continued

| Synthesis Example | Polymer[1] | PEO copolymerization ratio (wt. %) | Number-average molecular weight | $\eta_{sp/c}$ | $\delta^{[2]}$ |
|---|---|---|---|---|---|
| 8 | PEO3000(60)-co-PPES(40) | 60 | 32,500 | 1.53 | 10.62 |
| 9 | PEO3000(60)-co-PES(40) | 60 | 29,000 | 1.25 | 11.25 |
| 10 | PEO3000(60)-co-PSFS(40) | 60 | 32,000 | 1.55 | — |
| 11 | PEO3000(60)-co-PMPES(40) | 60 | 27,000 | 1.10 | — |

[1] The structural formulae of the polymers are represented by the following formulae. "3000" of "PEO3000" denotes the number-average molecular weight of the polyoxyethylene component.
[2] Solubility parameter The density ρ and $\Sigma F_i$ of each of the polymers are 10.15 and 9895.82 [PEO3000(60)-co-PFS(40)], 10.34, 8727.09 [PEO3000(60)-co-PS(40)], 10.69, 8240.27 [PEO3000(60)-co-PPES(40)] and 10.15, 9895.82 [PEO$_{3000}$(60)-co-PES(40)], respectively.

-indicates that measurement was not made.

PEO-o-PFS

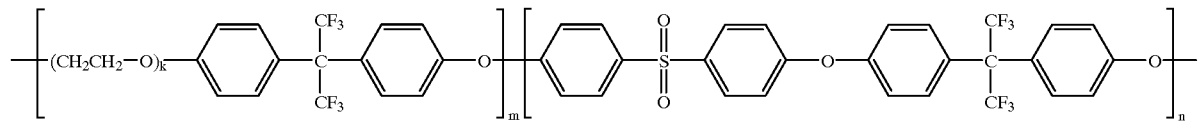

PEO-co-PSFS

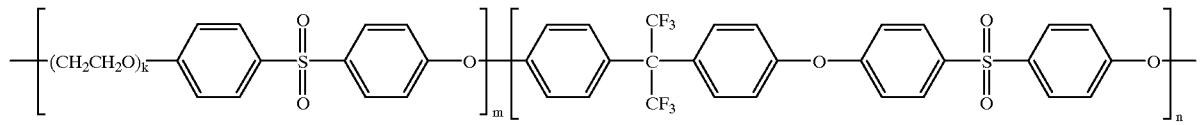

PEO-co-PES

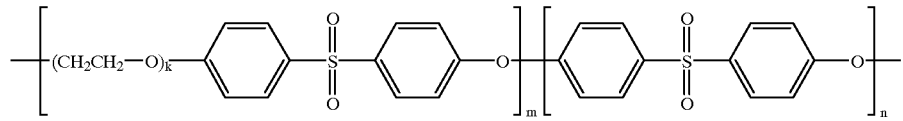

PEO-co-PPES

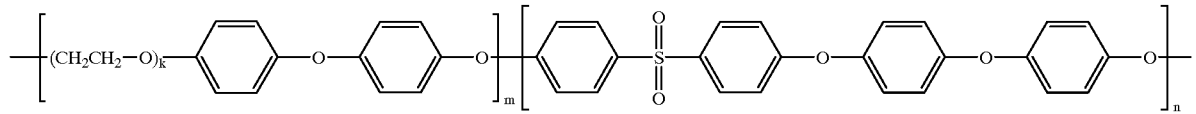

PEO-co-PMPES

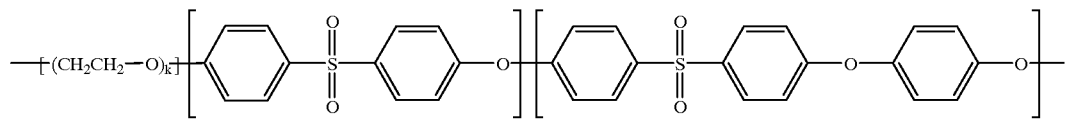

The poly(alkyl aryl ether)sulfone copolymer obtained in Synthetic Example 1 was dissolved in chloroform to prepare a dope solution at a concentration of 10% by weight. Onto a Teflon (E sheet mold form of a size 5 cm×5 cm, was cast 10 ml of the dope solution. The chloroform was then volatilized at normal temperature under atmospheric pressure for 24 hours, and the solution was further dried at 20° C. under 1 mmHg for 12 hours to afford a homogenous film. The copolymer was separately dissolved in N-methyl-2-pyrrolidone to provide a dope solution at a concentration of 10% by weight. Onto a Teflon® sheet mold form of a size 5 cm×5 cm, was cast 10 ml of the dope solution. The cast film was dipped in warm water at 30° C. to thereby extract and remove the N-methyl-2-pyrrolidone. The resulting film was further dried at 20° C. under 1 mmHg for 12 hours to prepare a homogenous porous film. All the films were self-supporting and had elastomeic elasticity without being broken by folding or pulling with hands. The films manifested hydrophilicity so as to be naturally wetted when brought into contact with water.

Furthermore, various poly(alkyl aryl ether)sulfone copolymers were prepared by the same operations as those described above, and the reduced viscosity and number-average molecular weight (Examples 2 to 4) were measured. The obtained results are collectively shown in the above Table 1. When films were molded from said copolymers in the same manner as that in the above Example 1, self-supporting homogeneous films could be obtained, respectively.

Examples 1 to 5

Evaluation of Antithrombogenic Properties of Poly(alkyl aryl ether)sulfone Copolymers (1) Preparation of Samples for Evaluation The poly(alkyl aryl ether)sulfone copolymers obtained in the above Synthesis Examples were respectively dissolved in chloroform to prepare dope solutions at a concentration of 1.0 wt. %. A sterilized polyethylene terephthalate (PET) disk (a diameter of 15 mm and a thickness of 0.5 mm) was immersed in 10 ml of each of the dope solutions. After 1 minute, the PET disk was taken out and allowed to stand in an atmosphere of a solvent overnight to thereby volatilize the solvent. Thereby, samples of the PET coated with the copolymers were prepared.

(2) Evaluation of Amount of Proteins Adsorbed

The amount of the proteins adsorbed on the above copolymers was spectroscopically determined when the samples prepared in (1) were brought into contact with a human platelet-poor plasma (PPP) solution. For evaluation, a prepared phosphoric acid buffer solution containing the PPP at a prescribed concentration (a phosphoric acid buffer solution at a concentration of 5% by weight) was brought into contact with the samples at 37° C. for 1 hour to extract the proteins adsorbed with an aqueous solution of sodium dodecyl sulfate at a concentration of % by weight. The amount of the proteins adsorbed was then estimated by the Micro BCA method. The number of the samples was 4 for each Example.

(3) Evaluation of the Amount of Platelets Adhered by Observation by SEM

Generally speaking, it is known that the kind of proteins adsorbed on the material surface and orientation thereof on the surface thereof greatly participate in the adhesion and aggregation of platelets which are the prestages of serious thrombogenesis. The activation of the platelets adhered (deformation and release of granules) affects the subsequent aggregation and thrombogenesis in the platelets and acceleration of a reaction of coagulation factor systems. Therefore, the degree of the compatibility of the material with blood can roughly be estimated by observing the state of platelets adhered on the material surface after the material is brought into contact with the blood (total blood or component blood). In this case, the state of platelets adhered to the surfaces of said copolymers after bringing the surfaces of the copolymers into contact with human platelet-rich plasma (PRP) used herein was observed by SEM. A supernatant obtained by adding 1/9 parts by volume of an aqueous solution of trisodium citrate at a concentration of 3.5% by weight to fresh blood collected from the vein of the human brachial part and centrifuging the mixture at 1,000 r.p.m. for 10 minutes was used as the PRP.

Samples coated with the above copolymers were then brought into contact with 0.7 ml of the PRP in a culture Petri dish (Falcon, 24 wells) at 37° C. for 3 hours. The samples were subsequently well washed with distilled water, fixed in an aqueous solution of glutaraldehyde at a concentration of 2.5% by weight at room temperature for 2 hours, freeze-dried and then subjected to gold vapor deposition to prepare observation samples (the samples were further freeze-dried after allowing thereof to stand at room temperature for 2 hours and then vapor of gold was deposited to give the observation samples). The resulting samples were used to count the number of the platelets adsorbed on the surface by SEM. The number of the samples was 2 for each Example.

Table 2 shows the amount of the proteins adsorbed and the number of platelets adhered. The case of a conventional aromatic polysulfone is shown as Comparative Example 1.

TABLE 2

| Example | Polymer | Amount of proteins adsorbed ($\mu$g/cm$^2$) | Number of platelets adhered (No./1,000 $\mu$m$^2$) |
| --- | --- | --- | --- |
| 1 | PEO3000(50)-co-PFS(50) | 0.50–0.60 | 2–9 |
| 2 | PEO3000(60)-co-PFS(40) | 0.42–0.49 | 1–3 |
| 3 | PEO2000(5)-co-PFS(50) | 0.55–0.62 | 3–10 |
| 4 | PEO2000(60)-co-PFS(40) | 0.45–0.52 | 2–5 |
| 5 | PEO3000(60)-co-PSFS(40) | 0.41–0.48 | 1–3 |
| Comparative Example 1 | PES | 1.16–1.36 | 70–85 |
| Referential Example 1 | PEO3000(50)-co-PES(50) | 0.43–0.50 | 3–5 |

PES:

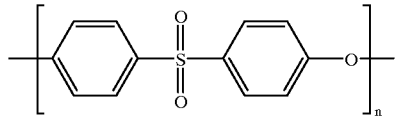

The above results definitely show that the poly(alkyl aryl ether)sulfone copolymers of the present invention have a smaller amount of proteins adsorbed and a smaller number of platelets adhered than those of a conventional aromatic polysulfone and are excellent in antithrombogenic properties.

Examples δ to 8 and Comparative Examples 2 to 4

Evaluation 1 of Antithrombogenic Properties of Polymer Compositions (1) Surface Analysis by ESCA The poly(alkyl aryl ether)sulfone copolymers (A) produced in Synthetic Examples 1 and 2 and cellulose triacetate (CTA) were dissolved in a prescribed mixing ratio in N-methyl-2-pyrrolidone (NMP) under heating to thereby prepare several kinds of dope solutions (a concentration of 10% by weight). The solutions were cast onto a Teflon® supporting substrate, and the solvent was then extracted with water to thereby provide membranes comprising the polymer compositions and having a thickness of about 0.5 mm. The concentrations of the above copolymers (A) in the vicinity of the surface of the membranes were analyzed by ESCA.

(2) Evaluation of Antithrombogenic Properties

The amount of proteins adsorbed and the number of platelets adhered were determined by the same manner as that in the above Examples 1 to 5. Hollow fiber membranes composed of the compositions were prepared according to the following method to evaluate the thrombogenesis suppressing ability.

(3) Preparation of hollow fiber membranes

Dope solutions (at a concentration of 13% by weight) of a cellulose triacetate composition of (1) described above were discharged from a nozzle and led to a coagulation bath comprising an aqueous solution containing NMP to thereby carry out diy jet-wet spinning. Thereby, homogeneous porous hollow fiber membranes were obtained.

was confirmed that the hollow fibers obtained by blend spinning the poly(alkyl aryl ether)sulfone copolymer (A) in an amount of 10% by weight based on the whole with the cellulose triacetate (B) almost completely suppressed the thrombogenesis (Example 7).

Hollow fibers described in European Patent Application No. EP 781795 and comprising polysulfones without containing fluorine formed thrombin for a contact time of 15 minutes, and thrombin were formed in all the hollow fibers after 4 hours (Comparative Examples 2 and 3).

No thrombus, however, was formed in Example 7 even for a contact time with blood of 4 hours, and high stability was manifested. Table 3 shows the results obtained in (1) to (3).

TABLE 3

| Example | Polymer (A) or (B) | Blend fraction of (B)/(A) (weight ratio) | Surface fraction of copolymer (A) (wt. %) | Amount of proteins adsorbed ($\mu$g/cm$^2$) | Number of platelets adhered (No./ 1,000 $\mu$m$^2$) | Number of formed thrombi (hollow fiber membranes/ in 40 hollow fiber membranes) After 15 min | After 4 h |
|---|---|---|---|---|---|---|---|
| Example 6 | PEO3000-(50)-co-PFS(50) | 95/5 | 55.3 | 0.57–0.67 | 5–10 | — | — |
| Example 7 | POE3000-(60)-co-PFS(40) | 90/10 | 85.7 | 0.51–0.63 | 3–9 | 0/40 | 0/40 |
| Example 8 | PEO3000-(60)-co-PSFS(40) | 90/10 | 67.2 | 0.49–0.59 | 4–7 | 0/40 | 0/40 |
| Com. Example 2 | PEO3000-(50)-co-PES(50) | 90/10 | 52.6 | 0.59–0.69 | 6–12 | 17/40 | 40/40 |
| Comp. Example 3 | PEO3000-(60)-co-PMPES(40) | 90/10 | 61.5 | 0.52–0.62 | 3–9 | 6/40 | Not measured. |
| Com. Example 4 | CTA | — | — | 1.11–1.15 | 60–85 | 40/40 | 40/40 |

Notes)
The mark — indicates that measurement was not made.
Com. Example means Comparative Example A bundle of the resulting 40 homogeneous hollow fiber membranes was dipped in nonheparin blood collected from the human brachial part and allowed to stand at normal temperature for 15 minutes and 4 hours. The hollow fiber membranes were then taken out and well washed with an aqueous solution of phosphoric acid buffer to subsequently observe the thrombogenesis state on the surfaces of the hollow fiber membranes. The evaluation was then made by counting the number of the hollow fiber membranes forming thrombin on the surfaces. Although the whole hollow fiber membranes were completely covered with thrombin in the case of the original triacetate (Comparative Example 4), it Examples 9 and 10 and Comparative Examples 5 and 6

Evaluation 2 of Antithrombogenic Properties of Polymer Compositions

Samples were prepared in the same manner as that in the above Examples 6 to 8, except that two kinds of polyvinyl chloride were used as the polymer (B) and tetrahydrofuran was used as the solvent, and surface analysis by the ESCA and evaluation of antithrombogenic properties were carried out. Table 4 shows the results.

TABLE 4

| Example | Polymer (B)/(A) | Blend fraction of (B)/(A) (weight ratio) | Surface fraction of copolymer (A) (wt. %) | Amount of proteins adsorbed ($\mu$g/cm$^2$) | Number of platelets adhered (No./1000 $\mu$m$^2$) | Shape factor of platelets adhered |
|---|---|---|---|---|---|---|
| Com. Example 5 | Hard PVC (H-PVC) | 100/0 | — | 1.23–1.38 | 68–75 | 2.56–3.25 |

TABLE 4-continued

| Example | Polymer (B)/(A) | Blend fraction of (B)/(A) (weight ratio) | Surface fraction of copolymer (A) (wt. %) | Amount of proteins adsorbed ($\mu$g/cm$^2$) | Number of platelets adhered (No./1000 $\mu$m$^2$) | Shape factor of platelets adhered |
|---|---|---|---|---|---|---|
| Example 9 | H-PVC/ PEO3000- (60)-co- PFS(40) | 90/10 | 59.3 | 0.44–0.60 | 1–13 | 1.00 |
| Com. Example 6 | Soft PVC (S-PVC) | 100/0 | — | 1.35–1.40 | 81–88 | 2.70–2.79 |
| Example 10 | S-PVC/ PEO3000- (60)-co- PFS(40) | 90/10 | 51.7 | 0.43–0.50 | 1–5 | 1.00 |

Notes)
Com. Example means Comparative Example

Examples 11 and 12 and Comparative Examples 7 and 8

Evaluation 3 of Antithrombogenic Properties of Polymer Compositions

Samples were prepared in the same manner as that in the above Examples 6 to 8, except that two kinds of polyurethanes (Pellethane 2363-80 M and AE Tecoflex 60®) were used as the polymer (B) and tetrahydrofuran (THF) was used as a solvent, and surface analysis by ESCA and evaluation of antithrombogenic properties were carried out. Table 5 shows the results.

TABLE 5

| Example | Polymer (B)/(A) | Blend fraction of (B)/(A) (weight ratio) | Surface fraction of copolymer (A) (wt. %) | Amount of proteins adsorbed ($\mu$g/cm$^2$) | Number of platelets adhered (No./1000 $\mu$m$^2$) | Shape factor of platelets adhered |
|---|---|---|---|---|---|---|
| Com. Example 7 | Pellethane 2363- 80AE ® (PU-1) | 100/0 | — | 1.33–1.41 | 78–93 | 2.42–2.87 |
| Example 11 | PU-1/ PEO3000- (60)-co- PFS(40) | 90/10 | 59.3 | 0.42–0.50 | 1–3 | 1.00 |
| Com. Example 8 | Tecoflex 60 ® (PU-2) | 100/0 | — | 1.05–1.17 | 75–85 | 2.10–2.25 |
| Example 12 | PU-2/ PEO3000- (60)-co- PFS(40) | 90/10 | 60.5 | 0.41–0.51 | 1–3 | 1.00 |

Notes)
Com. Example means Comparative Example

Examples 13 and 14 and Comparative Example 9

Evaluation 4 of Antithrombogenic Properties of Polymer Compositions

Samples and hollow fiber membranes were prepared in the same manner as in the above Examples 6 to 8, except that polymethyl methacrylate (PMMA) was used as the polymer (B). Surface analysis by ESCA and evaluation of the antithrombogenic properties were carried out. Table 6 shows the results.

TABLE 6

| Example | Polymer (A) or (B) | Blend fraction of (B)/(A) (weight ratio) | Surface fraction of copolymer (A) (wt. %) | Amount of proteins adsorbed ($\mu$g/cm$^2$) | Number of platelets adhered (No./1,000 $\mu$m$^2$) | Number of formed thromi (hollow fiber membranes/in 40 hollow fiber membranes) |
|---|---|---|---|---|---|---|
| 13 | PEO3000-(50)-co-PFS(50) | 90/10 | 61.3 | 0.57–0.67 | 7–15 | 0/40 |
| 14 | PEO3000-(60)-co-PFS(40) | 90/10 | 65.1 | 0.51–0.63 | 5–10 | 0/40 |
| Com. Example 9 | PMMA | 100/0 | — | 1.05–1.16 | 75–87 | 40/40 |

Notes)
Com. Example means Comparative Example

Examples 15 and 16 and Comparative Example 10

Evaluation 5 of Antithrombogenic Properties of Polymer Compositions

Samples and hollow fiber membranes were prepared in the same manner as that in the above Examples 6 to 8, except that the polysulfone (PES) was used as the polymer (B). Surface analysis by ESCA and evaluation of antithrombogenic properties were carried out. Table 7 the results.

The poly(alkyl aryl ether)sulfone copolymers produced in the above Example were melt blended with Tuftec H-1501® (a number-average molecular weight of 80,000 and a solubility parameter of $\delta$=8.2, manufactured by Asahi Chemical Industry Co., Ltd.) which was a typical styrene and rubber-based elastomer at 240° C. in a nitrogen gas stream to provide pellets of polymer compositions. The resulting pellets were then formed into filmy membranes under conditions of 160° C. and 40 kg/cm$^2$ with a pressurizing press.

TABLE 7

| Example | Polymer (A) or (B) | Blend fraction of (B)/(A) (weight ratio) | Surface fraction of copolymer (A) (wt. %) | Amount of proteins adsorbed ($\mu$g/cm$^2$) | Number of platelets adhered (No./1000 $\mu$m$^2$) | Number of formed thrombi (hollow fiber membranes/in 40 hollow fiber membranes) |
|---|---|---|---|---|---|---|
| Example 15 | PEO3000-(50)-co-PFS(50) | 90/10 | 60.2 | 0.55–0.66 | 7–12 | 1/40 |
| Example 16 | PEO3000-(60)-co-PFS(40) | 90/10 | 67.5 | 0.49–0.60 | 5–7 | 0/40 |
| Com. Example 10 | PES | 100/0 | — | 1.09–1.21 | 75–95 | 40/40 |

Notes)
Com. Example means Comparative Example

Examples 17 and 18 and Comparative Example 11

Evaluation 6 of Anthithrombogenic Properties of Polymer Ccompositions (1) Preparation of Samples for Evaluation The prepared films were finally treated in water at 70° C. for 2 hours to prepare specimen samples.

The samples were used to carry out surface analysis by ESCA and evaluation of antithrombogenic properties in the same manners as those described above. Table 8 shows the obtained results.

TABLE 8

| | Polymer (B)/(A) | Blend fraction of (B)/(A) (weight ratio) | Surface fraction of copolymer (A) (wt. %) | Amount of proteins adsorbed ($\mu$g/cm$^2$) | Number of platelets adhered (No./1000 $\mu$m$^2$) | Shape factor of platelets adhered |
|---|---|---|---|---|---|---|
| Example 17 | PEO3000-(60)-co-PFS(40) | 90/10 | 57.5 | 0.54–0.65 | 1–7 | 1.00–1.50 |
| Example 18 | PEO3000-(50)-co-PFS(50) | 90/10 | 52.6 | 0.58–0.66 | 3–8 | 1.00–1.50 |

TABLE 8-continued

| | Polymer (B)/(A) | Blend fraction of (B)/(A) (weight ratio) | Surface fraction of copolymer (A) (wt. %) | Amount of proteins adsorbed ($\mu g/cm^2$) | Number of platelets adhered (No./1000 $\mu m^2$) | Shape factor of platelets adhered |
|---|---|---|---|---|---|---|
| Com. Example 11 | Tuftec ® | 100/10 | — | 1.32–1.43 | 75–91 | 2.39–2.59 |

Notes)
Com. Example means Comparative Example

The above results definitely show that the poly(alkyl aryl ether)sulfone copolymers containing fluorine atoms of the present invention are present on the surfaces at a high concentration in the polymer compositions comprising the copolymers and the polymer compositions are excellent in the ability to suppress the adsorption of proteins and significantly suppress even the adhesion of platelets.

Example 19 and Comparative Example 12

Evaluation of Hollow Fiber Membranes as Hemodialysis Membranes

Ten thousand hollow fiber membranes composed of the polymer compositions comprising the poly(alkyl aryl ether) sulfone copolymers and cellulose triacetate and prepared in the above Examples 6 to 8 were bundled and then stored in a hemodialyzer case. The terminals were sealed with a urethane to provide a hemodialysis module. The resulting module was used to carry out various measurements such as water permeability (UFR) and clearance of dextran having a molecular weight of 10,000 (DA 10,000) and make evaluation thereof as dialysis performances.

Specific measuring conditions are described as follows:

(1) UFR: A bovine blood plasma containing citric acid added as an anticoagulant thereto was used and passed from the end face on one side of the hollow fiber bundle in the dialyzer at a flow velocity of 200 ml/min and filtered through the hollow fiber membranes at a rate of 15 ml/min. The differential pressure between the interior and the exterior of the membranes at this time was measured per minute to calculate the UFR.

(2) DA 10,000: An aqueous solution of dextran having a molecular weight of 10,000 at a concentration of 0.02% by weight was passed from the end face on one side of the hollow fiber bundle in the dialyzer to the other end face at a flow velocity of 200 ml/min and the concentration difference of the aqueous solution of the dextran (the molecular weight of 10,000) between the inlet and the outlet was obtained at this time to determine the DA 10,000.

(3) DA phosphorus: An aqueous solution containing 0.576 g/l of $Na_2HPO_4$, 0.12 g/l of $NaH_2PO_4$ and 9 g/l of NaCl dissolved therein was passed from the end face on one end of the hollow fiber bundle in the dialyzer to the other end face at a flow velocity of 200 ml/min and the concentration difference of phosphate ions between the inlet and the outlet was obtained at this time to determine the DA phosphorus.

4) SC 70,000: An aqueous solution of dextran having a molecular weight of 70,000 at a concentration of 0.01% by weight was passed from the end face on one side of the hollow fiber bundle in the dialyzer at a flow velocity of 200 ml/min and filtered through the hollow fiber membranes at a rate of 15 ml/min. The concentration of the dextran (the molecular weight of 70,000) of the resulting liquid was measured per minute to calculate the SC 70,000.

(5) SCALB: A bovine blood plasma containing citric acid as an anticoagulant added thereto was used and passed from the end face on one end of the hollow fiber bundle in the dialyzer at a flow velocity of 200 ml/min and filtered through the hollow fiber membranes at a rate of 15 l/min. The concentration of the dextran (a molecular weight of 70,000) of the resulting liquid was measured per minute to calculate the SCALB.

Table 9 shows the results of evaluation of performances as hemodialysis membranes. There was no great difference in performances among the hollow fibers prepared by spinning a conventional triacetate (Comparative Examples 12 and 13), hollow fibers comprising the sulfone copolymer without containing fluorine atoms in an amount of 10% by weight based on the whole in cellulose triacetate (Comparative Example 14) and hollow fibers obtained by blend spinning of the poly(alkyl aryl ether)sulfone copolymer (A) containing fluorine atoms in an amount of 10% by weight based on the whole with cellulose triacetate (B) (Examples 19 and 20) within the practical range.

TABLE 9

| Example | Polymer (A) or (B) | Blend fraction of (B)/(A) (weight ratio) | SC 70,000 | DA 10,000 | DA phosphorus | UFR | SCalb |
|---|---|---|---|---|---|---|---|
| Com. Example 12 | CTA | 100/0 | 0.156 | 62 | 184 | 37.0 | 0.005 |
| Com. Example 13 | CTA | 100/0 | 0.058 | 52 | — | — | — |
| Com. Example 14 | PEO3000-(50)-co-PES(50) | 90/10 | 0.103 | 61 | — | 34 | 0.010 |

TABLE 9-continued

| Example | Polymer (A) or (B) | Blend fraction of (B)/(A) (weight ratio) | SC 70,000 | DA 10,000 | DA phosphorus | UFR | SCalb |
|---|---|---|---|---|---|---|---|
| Example 19 | PEO3000-(50)-co-PFS(50) | 90/10 | 0.128 | 60 | 178 | 37.0 | 0.007 |
| Example 20 | PEO3000-(50)-co-PFS(50) | 90/10 | 0.079 | 53 | — | — | — |

Note)
The mark — indicates that measurement was not made.
Liquid paraffin was used as a core liquid at the time of spinning in Example 20.
Water was used in other cases.
Com. Example means Comparative Example.

The obtained results definitely show that medical hollow fiber membranes capable of retaining membrane characteristics essentially possessed by cellulose triacetate and excellent in blood compatibility can be provided by wet spinning compositions comprising the poly(alkyl aryl ether)sulfone having fluorine atoms and cellulose triacetate of the present invention.

What is claimed is:

1. A medical material for use in contact with blood, excellent in antithrombogenic properties, the material comprising a poly(alkyl aryl ether)sulfone copolymer (A) and a thermoplastic polymer (B) other than the copolymer (A), wherein the concentration of said copolymer (A) in the vicinity of the surface of a portion at least having a surface for use in contact with blood is at least 40% by weight, and said copolymer (A) is a fluorine atom-containing poly(alkyl aryl ether)sulfone copolymer (A) substantially comprising (a) constituent units represented by the following formulae (1) to (3):

  (1)

  (2)

  (3)

(in which $Ar^1$ and $Ar^2$ are each independently a bivalent aromatic group having 6 to 30 carbon atoms which may have a substituent group; $Ar^3$ and $Ar^4$ are each independently a bivalent aromatic group having 6 to 30 carbon atoms which may have a substituent group; Y is an alkylene group having 1 to 18 carbon atoms, at least one of its hydrogen atoms being substituted with a fluorine atom; R is an alkylene group having 2 or 3 carbon atoms or a combination of an alkylene group having 2 or 3 carbon atoms and an alkylene group having 4 carbon atoms; and k is a numeral which ensures that the molecular weight of a unit represented by —(—RO—)$_k$— is in the range of 400 to 20,000), the constituent unit represented by the above formula (3) accounting for 10 to 90% by weight based on the total amount of the constituent units represented by the above formulae (1), (2) and (3), the constituent unit represented by the above formula (1) accounting for 30 to 60 mole % based on the constituent unit represented by the above formula (2), and the copolymer having a reduced viscosity of at least 0.5 dl/g measured at a concentration of 1.2 g/dl in a mixed solvent of phenol and 1,1,2,2-tetrachloroethane at a weight ratio of 6/4 at 35° C.

2. The medical material as defined in claim 1, wherein Y is an alkylene group having 2 to 6 carbon atoms in which at least one of the hydrogen atoms is substituted with fluorine atom in the above formula (2).

3. The medical material as defined in claim 1, wherein $Ar^1$, $Ar^2$, $Ar^3$ and $Ar^4$ are each independently a bivalent aromatic hydrocarbon group having 6 to 10 carbon atoms which may have a substituent group in the above formulae (1) and (3), and R is an ethylene group.

4. The medical material as defined in claim 1, wherein the above medical material comprises a polymer composition comprising 1 to 50% by weight of the copolymer (A) and 99 to 50% by weight of the polymer (1).

5. The medical material as defined in claim 1, wherein the above medical material is composed of a polymer composition comprising 5 to 20% by weight of the copolymer (A) and 95 to 80% by weight of the polymer (B) and the concentration of the copolymer (A) in said vicinity of the surface is 50 to 90% by weight.

6. The medical material as defined in claim 1, wherein the medical imaterial is a hollow fiber for artificial kidneys, a hollow fiber for artificial lungs, a catheter, an artificial blood vessel, a blood-collecting tube, a tube for blood circuits, a blood container, a hemodialysis membrane, a blood plasma separating membrane or a medical suture thread.

7. The medical material as defined in claim 1, wherein the thermoplastic polymer (B) other than the copolymer (A) can be dissolved in the same solvent that dissolves the above copolymer (A).

8. The medical material as defined in claim 7, wherein the thermoplastic polymer (B) other than the copolymer (A) is at least one selected from the group consisting of cellulose triacetate, a polysulfone, a polyaryl ether sulfone, polyvinyl chloride, a polyurethane and polymethyl methacrylate.

9. The medical material as defined in claim 1, wherein the amount of proteins adsorbed is 0.8 $\mu g/cm^2$ or below measured by the Micro BCA method when brought into contact with a human blood plasma at 37° C. for 1 hour.

10. The medical material as defined in claim 1, wherein the medical material is a hollow fiber membrane and the number of the hollow fiber membranes forming thrombin on the surface is 10% or below based on the whole when dipping the plural hollow fiber in nonheparin blood collected from the human brachial part at normal temperature for 4 hours and then washing the hollow fiber membranes.

11. A medical material for use in contact with blood, excellent in antithrombogenic properties, the material composed of a polymer composition comprising 5 to 20% by weight of a poly(alkyl aryl ether)sulfone copolymer (A) and 95 to 80% by weight of a thermoplastic polymer (B) other than the copolymer (A), wherein the concentration of said copolymer (A) in the vicinity of the surface of a portion at least having a surface for use in contact with blood is 50 to 90% by weight, and said polymer (A) is a fluorine atom-containing poly(alkyl aryl ether)sulfone copolymer substantially comprising (a) constituent units represented by the following formulae (11) to (31):

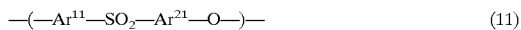  (11)

  (21)

  (31)

(in which $Ar^{11}$ and $Ar^{21}$ are each independently a bivalent aromatic hydrocarbon group having 6 to 10 carbon atoms which may have a substituent group; $Ar^{31}$ and $Ar^{41}$ are each independently a bivalent aromatic hydrocarbon group having 6 to 10 carbon atoms which may have a substituent group; Y is an alkylene group having 2 to 6 carbon atoms, at least one of its hydrogen atoms being substituted with a fluorine atom; R is an ethylene group; and k is a numeral which ensures that the molecular weight of a unit represented by —(—RO—)$_k$— is in the range of 400 to 20,000), the constituent unit represented by the above formula (3) accounting for 30 to 70% by weight based on the total amount of the constituent units represented by the above formulae (11), (21) and (31), the constituent unit represented by the above formula (11) accounting for 30 to 60 mole % based on the constituent unit represented by the above formula (21), the above copolymer (A) having a reduced viscosity of at least 0.5 dl/g measured at a concentration of 1.2 g/dl in a mixed solvent of phenol and 1, 1,2,2-tetrachloroethane at a weight ratio of 6/4 at 35° C., and said thermoplastic polymer (B) is (b) at least one selected from the group consisting of cellulose triacetate, a polysulfone, a polyaryl ether sulfone, polyvinyl chloride, a polyurethane and polymethyl methacrylate.

12. The medical material as defined in claim 11, wherein the amount of proteins adsorbed is 0.7 μg/cm$^2$ or below measured by the Micro BCA method when brought into contact with a human blood plasma at 37° C. for 1 hour.

13. The medical material as defined in claim 11, wherein the medical material is a hollow fiber membrane and the number of the hollow fiber membranes forming thrombin on the surface is 10% or below based on the whole when dipping the plural hollow fiber membrane in nonheparin blood collected from the human brachial part at normal temperature for 4 hours and then washing the hollow fiber membranes.

14. (After the amendment) A fluorine atom-containing poly(alkyl aryl ether)sulfone copolymer suitable for a medical material for use in contact with blood substantially comprising (a) constituent units represented by the following formulae (1) to (3):

  (1)

  (2)

  (3)

(in which $Ar^1$ and $Ar^2$ are each independently a bivalent aromatic group having 6 to 30 carbon atoms which may have a substituent group; $Ar^3$ and $Ar^4$ are each independently a bivalent aromatic group having 6 to 30 carbon atoms which may have a substituent group; Y is an alkylene group having 1 to 18 carbon atoms, at least one of its hydrogen atoms being substituted with a fluorine atom; R is an alkylene group having 2 or 3 carbon atoms or a combination of an alkylene group having 2 or 3 carbon atoms with an alkylene group having 4 carbon atoms; and k is a numeral which ensures that the molecular weight of a unit represented by —(—RO—)$_k$— is in the range of 400 to 20,000 ), the constituent unit represented by the above formula (3) accounting for 10 to 90% by weight based on the total amount of the constituent units represented by the above formulae (1), (2) and (3), the constituent unit represented by the formula (1) accounting for 30 to 60 mole % based on the constituent unit represented by the above formula (2), and the copolymer having a reduced viscosity of at least 0.5 dl/g measured at a concentration of 1.2 g/dl in a mixed solvent of phenol and 1,1,2,2-tetrachloroethane at a weight ratio of 6/4 at 35° C.

15. The fluorine atom-containing poly(alkyl aryl ether) sulfone copolymer as defined in claim 14, wherein Y is an alkylene group having 2 to 6 carbon atoms in which at least one of hydrogen atoms is substituted with a fluorine atom in the above formula (2).

16. The fluorine atom-containing poly(alkyl aryl ether) sulfone copolymer having fluorine atoms as defined in claim 14, wherein $Ar^1$, $Ar^2$, $Ar^3$ and $Ar^4$ are each independently a bivalent aromatic hydrocarbon group having 6 to 10 carbon atoms which may have a substituent group and R is an ethylene group in the above formulae (1) to (3).

17. The fluorine atom-containing poly(alkyl aryl ether) sulfone copolymer as defined in claim 14, wherein the amount of proteins adsorbed is 0.7 μg/cm$^2$ or below measured by the Micro BCA method when brought into contact with a human blood plasma at 37° C. for 1 hour.

18. A method for producing a medical material which comprises the steps of:

preparing a dope comprising a fluorine atom-containing poly(alkyl aryl ether)sulfone copolymer (A) substantially comprising (a) constituent units represented by the following formulae (1) to (3):

  (1)

  (2)

  (3)

(in which $Ar^1$ and $Ar^2$ are each independently a bivalent aromatic group having 6 to 30 carbon atoms which may have a substituent group; $Ar^3$ and $Ar^4$ are each independently a bivalent aromatic group having 6 to 30 carbon atoms which may have a substituent group; Y is an alkylene group having 1 to 18 carbon atoms in which at least one of hydrogen atoms is substituted with fluorine atom; R is an alkylene group having 2 or 3 carbon atoms or a combination of an alkylene group having 2 or 3 carbon atoms with an alkylene group having 4 carbon atoms; and k is a numeral which ensures that the molecular weight of a unit represented by —(—RO—)k— is in the range of 400 to 20,000 ), the constituent unit represented by the above formula (3) accounting for 10 to 90% by weight based on the total amount of the constituent units represented by the above formulae (1), (2) and (3), the constituent unit represented by the above formula (1) accounting for 30 to 60 mole % based on the constituent unit represented by the above formula (2), and the copolymer having a reduced viscosity of at least 0.5 dL/g measured at a concentration of 1.2 g/dL in a mixed solvent of phenol and 1,1,2,2-tetrachloroethane at a weight ratio of 6/4 at 35° C., a thermoplastic polymer (B) other than the copolymer (A) and an aprotic polar organic solvent (C) capable of dissolving the copolymer (A) and the polymer (B) at the total concentration of the above components (A) and (B) of 1 to 30% by weight;

forming the dope into a thin membrane; and subjecting the thin membrane to wet or dry molding method to produce a medical material having a 1 mm or less thick portion for contact with blood.

19. The method for producing the medical material as defined in claim 18, wherein the thermoplastic polymer (B) is cellulose triacetate.

20. The method for producing the medical material as defined in claim 18, wherein the medical material is a hollow fiber membrane.

21. The method for producing the medical material as defined in claim 18, wherein the aprotic polar organic solvent is at least one selected from the group consisting of tertrahydrofuran, 1,3-dioxolane, 1,4-dioxane, dimethylformamide, dimethylacetamide, N-methyl-2-pyrrolidone, dimethyl sulfoxide, methylene chloride and chloroform.

* * * * *